(12) United States Patent
Kawase et al.

(10) Patent No.: US 8,212,059 B2
(45) Date of Patent: Jul. 3, 2012

(54) PROCESS FOR PRODUCING VITAMIN D DERIVATIVE USING PHOTOREACTION

(75) Inventors: Akira Kawase, Tokyo (JP); Yasuharu Kato, Shizuoka (JP); Kazutomo Kinoshita, Shizuoka (JP); Yasushi Kitoh, Kanagawa (JP); Takuma Ikeda, Tokyo (JP); Tsuyoshi Haneishi, Tokyo (JP); Noriaki Maruyama, Tokyo (JP); Mio Kobayashi, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 901 days.

(21) Appl. No.: 12/095,734

(22) PCT Filed: Nov. 30, 2006

(86) PCT No.: PCT/JP2006/323891
§ 371 (c)(1),
(2), (4) Date: May 30, 2008

(87) PCT Pub. No.: WO2007/063930
PCT Pub. Date: Jun. 7, 2007

(65) Prior Publication Data
US 2010/0261917 A1      Oct. 14, 2010

(30) Foreign Application Priority Data
Nov. 30, 2005    (JP) .................................. 2005-346356

(51) Int. Cl.
C07C 401/00        (2006.01)
C07J 21/00         (2006.01)

(52) U.S. Cl. ......................................... 552/653; 540/46

(58) Field of Classification Search .................... 540/46; 552/610, 653
See application file for complete search history.

(56) References Cited

U.S. PATENT DOCUMENTS
6,184,398 B1      2/2001    Kawase
2003/0195176 A1   10/2003   Kawase et al.
2004/0019023 A1   1/2004    Morikawa et al.

FOREIGN PATENT DOCUMENTS
EP        1295871 A1 *   3/2003

* cited by examiner

*Primary Examiner* — Barbara P Badio
(74) *Attorney, Agent, or Firm* — Browdy and Niemark, PLLC

(57) ABSTRACT

There are provided a novel process for producing [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, which process is characterized by irradiating a compound represented by the formula:

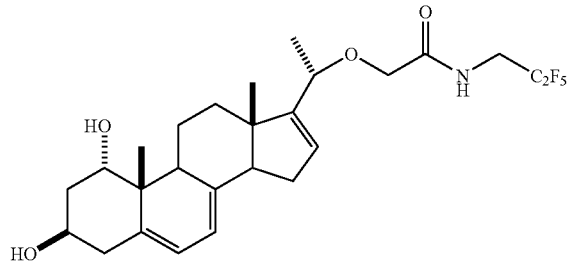

with UV to ring-open the compound, and then isomerizing the resulting compound; an intermediate useful for carrying out the process; and a process for producing the intermediate.

6 Claims, No Drawings

PROCESS FOR PRODUCING VITAMIN D DERIVATIVE USING PHOTOREACTION

The present invention relates to a novel process for producing a vitamin D derivative useful as a pharmaceutical, to an intermediate useful for carrying out the process, and to a process for producing the intermediate.

BACKGROUND ART

The vitamin D derivative represented by Formula (1):

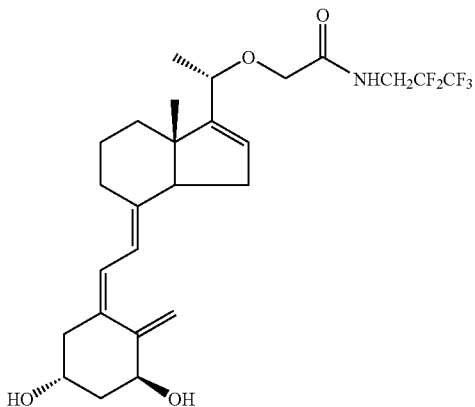

(1)

(chemical name: [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, or [{1α,3β-dihydroxy-9,10-secopregna-5,7,10(19),16-tetraen-20(S)-yl}oxy]-N-(2,2,3,3,3-pentafluoropropyl)acetamide, or N-(2,2,3,3,3-pentafluoropropyl)-[{(1S,3R,5Z,7E,20S)-1,3-dihydroxy-9,10-secopregna-5,7,10(19),16-tetraen-20-yl}oxy]acetamide) exhibits useful human keratinocyte growth inhibition activity while its harmful calcium level-raising activity is lower than the conventional vitamin D derivatives, so that it is useful as a therapeutic agent for skin disorders such as psoriasis.

As a process for producing this compound, a process is known, in which [{1α,3β-bis(tert-butyldimethylsilyloxy)-9,10-secopregna-5,7,10(19),16-tetraen-20(S)-yl}oxy]acetic acid is reacted with 2,2,3,3,3-pentafluoropropylamine. See WO 2001/096293 (Patent Literature 1).

Patent Literature 1: WO 2001/096293

DISCLOSURE OF THE INVENTION

Problems to be Solved by the Invention

However, the above-described conventional process has a problem in that a carbon monoxide-inserting reaction is necessary for obtaining (1S,3R,20S)-1,3-bis(tert-butyldimethylsilyloxy)-20-hydroxypregna-5,7,16-triene which is an intermediate in the process, which problem can be an obstacle in scaling up the conventional process. Further, in addition thereto, the conventional process has various problems which can be obstacles in scaling up the process, such as that the reactions must be carried out at a temperature not higher than −15° C. since the stereoselectivity over the reactions carried out in the conventional process is sensitive to a temperature. Therefore, development of a more practical process is desired. Further, the above-described conventional process is not satisfactory in the yield, number of steps and so on in the production of the vitamin D derivative represented by Formula (1) from the above-described intermediate, so that development of a more efficient process is also desired.

The present invention was made under the above-described circumstances. Accordingly, an object of the present invention is to provide a practical and efficient process for producing [{(5Z,7E)-(1S,3R,20S)-1,3-dihydroxy-9,10-secopregna-5,7,10(19), 16-tetraen-20-yl}oxy]-N-(2,2,3,3,3-pentafluoropropyl)acetamide.

Means for Solving the Problems

As a result of extensive research for attaining the above-described object, it has been found that the desired compound can be efficiently produced by irradiating the compound represented by Formula (2):

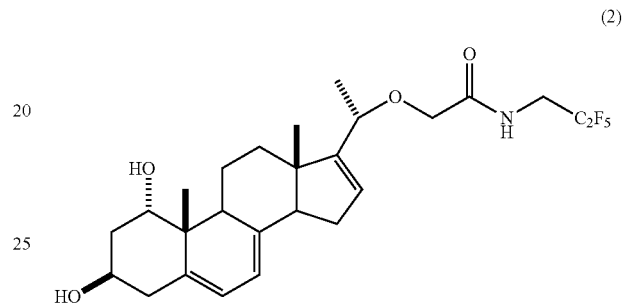

(2)

with UV to open the B-ring of the steroid skeleton of the compound; and then isomerizing the resulting compound.

Therefore, the present invention provides a novel process for producing the compound represented by Formula (1):

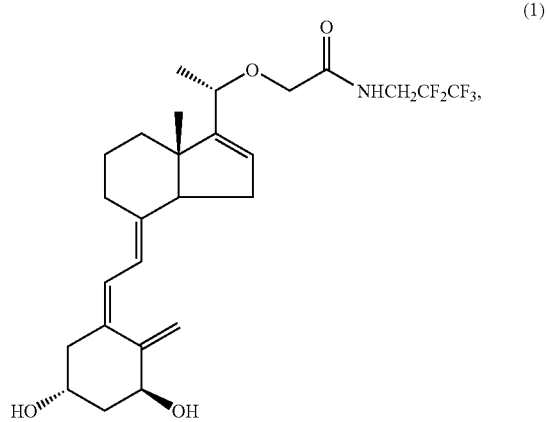

(1)

comprising the steps of:
irradiating a compound represented by Formula (2):

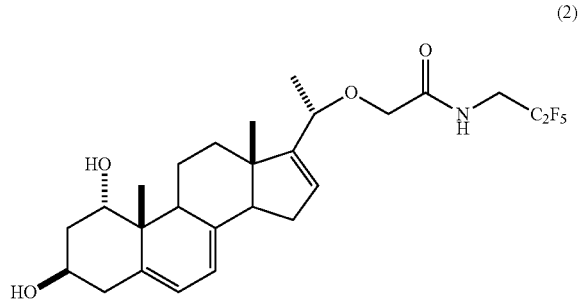

(2)

with UV to open the B-ring of the steroid skeleton of the compound; and isomerizing the resulting compound to obtain the compound of Formula (1).

In a preferred embodiment, the compound represented by Formula (2) is obtained by a process comprising the steps of:

subjecting a compound represented by Formula (3):

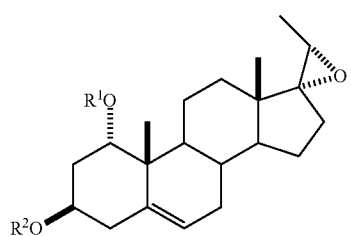

(3)

(wherein $R^1$ and $R^2$, which may be the same or different, are each a substituted silyl group)

to a formation of a conjugated diene in the B-ring of the steroid skeleton of the compound;

subjecting the resulting compound to a formation of an allyl alcohol moiety via ring-opening of the epoxy group to obtain a compound represented by Formula (4):

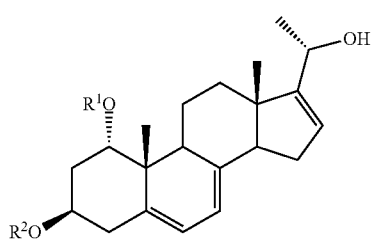

(4)

reacting the obtained compound with 2-bromo-N-(2,2,3,3,3-pentafluoropropyl)acetamide to obtain a compound represented by Formula (5):

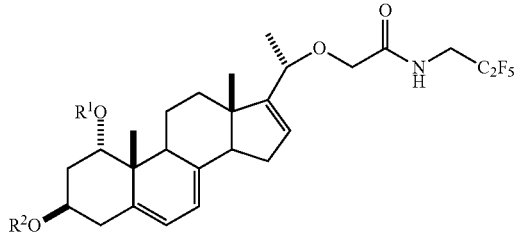

(5)

replacing $R^1$ and $R^2$ of the obtained compound with hydrogen atoms, respectively.

In another preferred embodiment, the compound represented by Formula (2) is obtained by a process comprising the steps of:

reacting a compound represented by Formula (4):

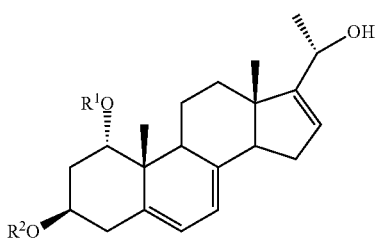

(4)

(wherein $R^1$ and $R^2$, which may be the same or different, are each a substituted silyl group)
with 2-bromo-N-(2,2,3,3,3-pentafluoropropyl)acetamide to obtain a compound represented by Formula (5):

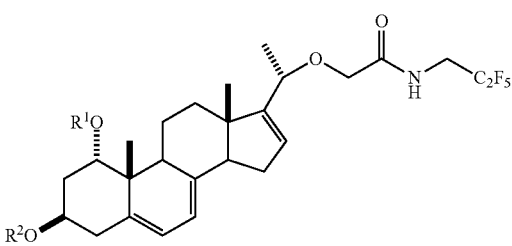

(5)

replacing $R^1$ and $R^2$ of the obtained compound with hydrogen atoms, respectively.

The main intermediates used in the above-described process, that is, the compound represented by Formula (2):

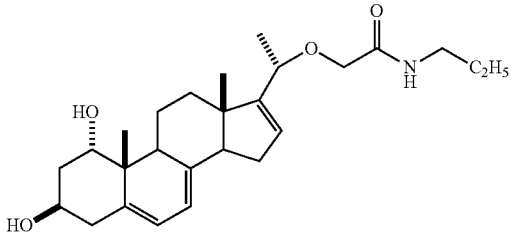

(2)

and the compound represented by Formula (3):

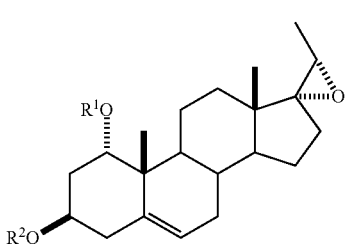

(3)

(wherein $R^1$ and $R^2$, which may be the same or different, are each a substituted silyl group) are novel.

Therefore, the present invention also provides the compound of Formula (2) and the compound of Formula (3).

In the present invention, the substituents in the "substituted silyl group" are selected from $C_1$-$C_7$ linear or branched alkyl groups, phenyl groups optionally substituted with one of more linear or branched $C_1$-$C_3$ alkyl groups, or phenylalkyl groups (the alkyl groups in the phenylalkyl group are each $C_1$-$C_5$ linear or branched alkyl group, and the phenyl group in the phenyl alkyl group is optionally further substituted with one of more $C_1$-$C_3$ linear or branched alkyl groups). Examples of the $C_1$-$C_7$ linear or branched alkyl groups include methyl group, ethyl group, n-propyl group, i-propyl group, n-butyl group, sec-butyl group, tert-butyl group, n-pentyl group, n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethylpropyl group (thexyl group), n-heptyl group and the like. Examples of the phenyl group optionally substituted with one of more linear or branched $C_1$-$C_3$ alkyl groups include phenyl group, tolyl group, ethylphenyl group and the like. Examples of the above-described phenylalkyl group include benzyl group, phenethyl group, xylyl group and the like.

"Substituted silyl group" means a tri-substituted silyl group which is substituted with 3 substituents arbitrarily selected from the above-mentioned substituents. Combination of the 3 substituents may be any of the cases where all of them are the same, all of them are different, and two of them are the same and one is different therefrom. The cases where all of them are the same or two of them are the same and one is different therefrom are preferred, and the cases where two of them are the same and one is different therefrom are more preferred.

Specific examples of the "substituted silyl group" include trimethylsilyl group, triethylsilyl group, triisopropylsilyl group, dimethylisopropylsilyl group, diethylisopropylsilyl group, dimethylthexylsilyl group, tert-butyldimethylsilyl group, tert-butyldiphenylsilyl group, tribenzylsilyl group, tri-p-xylylsilyl group, triphenylsilyl group, diphenylmethylsilyl group and tert-butylmethoxyphenylsilyl group. Among these groups, tert-butyldimethylsilyl group (hereinafter also referred to as "TBS" group) is preferred.

$R^1$ and $R^2$, which are each "substituted silyl group", may be the same or different. Preferably, they are the same group, and more preferably, both of them are TBS groups.

In a preferred embodiment of the present invention, the process of the present invention is carried out according to the reaction steps shown in Scheme 1 below.

Scheme 1:

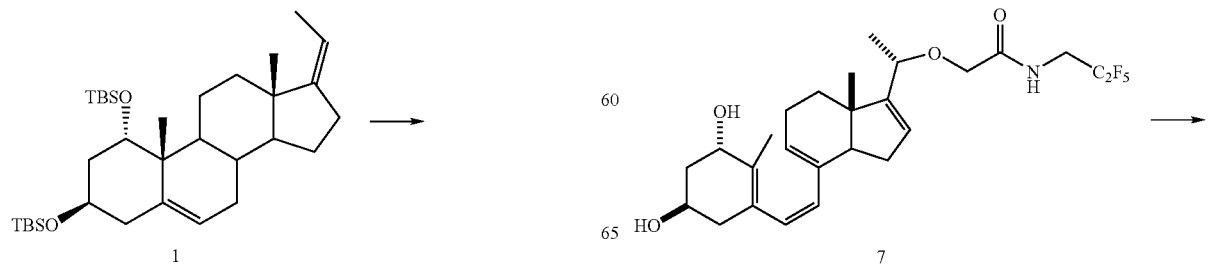

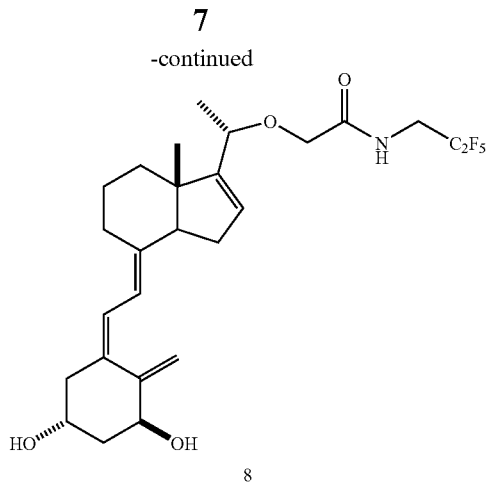

8

Among the intermediates shown in Scheme 1, the compound of Formula (6):

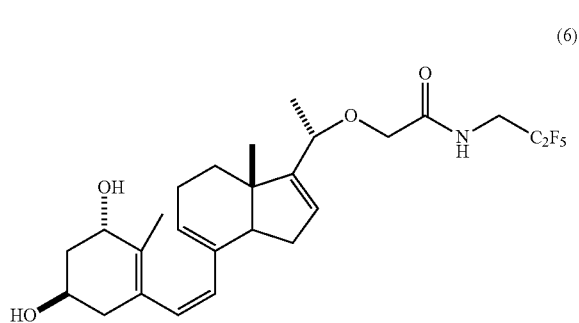

is also novel.

Therefore, the present invention also provides the compound of Formula (6).

Each of the reaction steps shown in the above-described Scheme will now be explained.

<Compound 1→Compound 2>

Compound 1 is a known substance, and can be synthesized according to the method described in, for example, Chem. Pharm. Bull., 40(5), 1120-4 (1992), Org. Process. Res. Dev., 2005, 9, 278-287; JP 5-19094 A; or the like.

Compound 2 (the compound represented by the above-described Formula (3)) can be obtained by epoxidizing Compound 1. This epoxidation is carried out by, for example, reacting Compound 1 with a suitable epoxidizing agent in a suitable solvent in the presence of, if necessary, a catalyst, for usually 5 minutes to 10 hours, preferably 2 hours to 4 hours. Examples of the epoxydizing agent include peracids such as m-chloroperbenzoic acid, perbenzoic acid, peracetic acid, magnesium monoperoxyphthalate; and hydroperoxides such as hydrogen peroxide and tert-butylhydroperoxide. Among these epoxydizing agents, peracids such as m-chloroperbenzoic acid and magnesium monoperoxyphthalate are preferred, and in view of avoiding side reactions and ease of purification of the product in the next step, m-chloroperbenzoic acid is preferred. The amount of the epoxidizing agent to be used is appropriately selected taking the reactivity of the substrate having a double bond into consideration, and is usually 1 to 3 equivalents, preferably 1.1 to 1.5 equivalents with respect to Compound 1. Examples of the solvent to be used include halogenated solvents such as dichloromethane, chloroform, bromoform, carbon tetrachloride and carbon tetrabromide; hydrocarbon solvents such as n-pentane, n-hexane, cyclohexane, n-heptane, n-octane, toluene and xylene; acetate solvents such as methyl acetate, ethyl acetate, n-propyl acetate, i-propyl acetate and t-butyl acetate; nitrile solvents such as acetonitrile, benzonitrile and benzyl cyanide; alcohol solvents such as methanol, ethanol, n-propanol, i-propanol and n-butanol; and water. These solvents may be used individually or in combination. From the viewpoint of ease of checking the reaction progress, using ethyl acetate alone or the combination of ethyl acetate and acetonitrile is preferred, and from the viewpoint of simplicity of the operation, using ethyl acetate alone is preferred. Although examples of the catalyst which may be present in the reaction system as required include inorganic alkali salts, organic amines, vanadium complexes, titanium alkoxides, tartaric acid esters and the like, the catalyst is preferably not present. The reaction temperature is usually −50° C. to +50° C., and in view of the reactivity and safety, the reaction temperature is preferably 10° C. to 25° C. The unreacted epoxidizing agent remained at the completion of the reaction may be inactivated by, for example, the treatment with a reducing agent.

In a preferred embodiment, epoxidation of Compound 1 is carried out by using m-chloroperbenzoic acid as an epoxidizing agent, using ethyl acetate and/or heptane, preferably ethyl acetate as a solvent, at a temperature between 10° C. and 30° C. for 2 to 4 hours.

<Compound 2→Compound 3>

Compound 3 can be obtained by subjecting the thus obtained Compound 2 to a reaction for formation of a conjugated diene in the B-ring of the steroid skeleton of Compound 2. The reaction for forming a conjugated diene in Compound 2 is carried out by brominating the methylene group at the 7-position in the B-ring of the steroid skeleton of Compound 2, and then dehydrobrominating the resulting group.

First, the bromination of Compound 2 can be attained by carrying out the reaction using a suitable brominating agent, in the presence of a radical initiator, in a suitable solvent for 5 minutes to 1 hour. Examples of the brominating agent include N-bromosuccinimide, 1,3-dibromo-5,5-dimethylhydantoin and the like, and N bromosuccinimide is preferred. The amount of the brominating agent is appropriately selected taking the reactivity of the substrate into consideration, and preferably 1.3 to 1.4 equivalents with respect to Compound 2. Examples of the radical initiator include benzoyl peroxide and 2,2'-azobis(isobutyronitrile) and the like, and 2,2'-azobis (isobutyronitrile) is preferred. The solvent to be used is not restricted as long as the side reactions are within the acceptable degree and it does not influence on the safety or the like, and examples thereof include hydrocarbon solvents such as n-pentane, n-hexane, cyclohexane, n-heptane, n-octane, toluene and xylene; and halogenated solvents such as dichloromethane, chloroform, bromoform, carbon tetrachloride and carbon tetrabromide. Preferred are hydrocarbon solvents, and more preferred is n-heptane. From the viewpoint of avoiding side reactions and/or decomposition of Compound 2, it is preferred to further add a base used in the next dehydrobromination step, which base is an organic amine such as triethylamine, diethylamine, diisopropylamine, pyridine, dimethylaminopyridine or γ-collidine, or an inorganic alkali salt such as sodium carbonate, potassium carbonate, sodium hydrogen carbonate, sodium hydroxide or calcium hydroxide. Among these bases, to add γ-collidine is especially preferred. The reaction temperature is usually −10° C. to 150° C., and in view of the reactivity and safety, the reaction temperature is preferably 0° C. to 100° C., more preferably 65° C. to 85° C. The reaction time is usually 3 minutes to 3 hours, preferably 5 minutes to 30 minutes.

In a preferred embodiment, bromination of Compound 2 is carried out by using N-bromosuccinimide as the brominating agent, using 2,2'-azobis(isobutyronitrile) as the radical initiator, adding γ-collidine, in n-heptane solvent at 70° C. to 80° C.

After the bromination, the product may be subjected to the dehydrobromination, which is the next reaction, without isolation and purification of the desired compound, and this is preferred.

The dehydrobromination after the bromination may be carried out by, for example, allowing the reaction in the presence of a base, in a hydrocarbon solvent such as n-pentane, n-hexane, cyclohexane, n-heptane, n-octane, toluene or xylene, preferably in toluene, at a temperature between room temperature and reflux temperature, preferably at a temperature between 110° C. and 120° C., for 30 minutes to 3 hours. The amount of the base to be used is appropriately selected taking the reactivity of the substrate into consideration, and preferably 3 to 4 equivalents with respect to Compound 2. In cases where the base added in the bromination step remains at the completion of the bromination step, the remaining base may be used as the base in this step to make it unnecessary to further add a base, and this is preferred from the viewpoint of efficiency, although a base may be further added in this step. The obtained Compound 3 is a known substance, and is described in, for example, WO 98/28266.

<Compound 3→Compound 4>

Compound 4 (the compound represented by the above-described Formula (4)) can be obtained by subjecting the thus obtained Compound 3 to a formation of an allyl alcohol moiety via ring-opening of the epoxy group. The formation of allyl alcohol moiety in Compound 3 via the ring-opening of the epoxy group can be carried out by allowing the reaction in the presence of a suitable Lewis acid in a catalytic amount or stoichiometric amount, preferably in an amount of 0.1 to 0.2 equivalents with respect to Compound 3, in a suitable solvent, at a temperature between room temperature and reflux temperature for 30 minutes to 3 hours. Examples of the Lewis acid which can be used include aluminum trialkoxides, aluminum chloride, titanium chloride and the like. Among these, aluminum trialkoxides are preferred, and aluminum isopropoxide is more preferred. The suitable solvent is not restricted as long as it does not influence the reaction, and examples thereof include hydrocarbon solvents such as n-pentane, n-hexane, cyclohexane, n-heptane, n-octane, toluene and xylene; and halogenated solvents such as dichloromethane, chloroform, bromoform, carbon tetrachloride and carbon tetrabromide. These solvents may be used individually or they may be used in combination. Among these solvents, use of a hydrocarbon solvent alone is preferred, and use of toluene alone is more preferred.

In a preferred embodiment, the formation of allyl alcohol moiety in Compound 3 via the ring-opening of the epoxy group is carried out in the presence of an aluminum trialkoxide in toluene at 110° C. to 120° C.

The above-described steps from Compound 2 to the obtainment of Compound 4 may be carried out in one pot as continuous reactions without isolating Compound 3, and this is preferred.

After bromination of Compound 2, the reactions with the base and with the Lewis acid may be carried out simultaneously, that is, the step of dehydrobromination in which Compound 3 is synthesized from Compound 2, and the step of obtaining Compound 4 from Compound 3 may be simultaneously carried out, and this is preferred.

Compound 4 is also a known substance and is described in, for example, WO 98/28266.

<Compound 4→Compound 5>

Compound 5 (the compound represented by the above-described Formula (5)) can be obtained by alkylating the hydroxyl group in the thus obtained Compound 4 using 2-halo-N-(2,2,3,3,3-pentafluoropropyl)acetamide. The alkylation of the hydroxyl group in Compound 4 is carried out by, for example, adding the above-described halo compound to Compound 4 to allow the reaction in the presence of a suitable base in a suitable solvent at a temperature between −80° C. and +10° C. Examples of the suitable base include the bases capable of carrying out deprotonation of hydroxyl group, including metal disilazides such as potassium bis(trimethylsilyl)amide, lithium bis(trimethylsilyl)amide and sodium bis(trimethylsilyl)amide; and metal hydrides such as sodium hydride, potassium hydride and calcium hydride. Among these, metal disilazides, particularly potassium bis(trimethylsilyl)amide is preferred. The amount of the base to be used is preferably 2 to 3 equivalents, more preferably 2.2 to 2.8 equivalents with respect to Compound 5. Examples of the "halo" in the above-described halo compound include chloro, bromo and iodo, and bromo is preferred. Suitable solvents include ether solvents such as tetrahydrofuran, dioxane and ether; and hydrocarbon solvents such as n-pentane, n-hexane, cyclohexane, n-heptane, n-octane, toluene and xylene. These solvents may be used individually or they may be used in combination, and from the viewpoint of avoiding side reactions, avoiding drastic elevation of the reaction temperature occurred when the above-described halo compound is added, decreasing the side products produced due to the elevation of temperature, and/or of shortening the time required until the completion of the addition of the above-described halo compound, combination of an ether solvent and a hydrocarbon solvent is preferred, and the combination of tetrahydrofuran and toluene is more preferred. The volume ratio of tetrahydrofuran to toluene in the reaction system is preferably 7:3 to 8:2. When the reaction is carried out at this volume ratio of solvents, there is an advantage in that the time required for the addition of the above-described halo compound is not likely to be influenced by the reaction scale.

In a preferred embodiment, alkylation of the hydroxyl group of Compound 4 is carried out using potassium bis(trimethylsilyl)amide in a mixed solvent of tetrahydrofuran and toluene at −10° C. to 0° C., and using as the halo compound 2-bromo-N-(2,2,3,3,3-pentafluoropropyl)acetamide (Compound 9) shown in Scheme 1.

The 2-halo-N-(2,2,3,3,3-pentafluoropropyl)acetamide may be obtained by reacting 2,2,3,3,3-pentafluoroamine with a haloacetic acid, a haloacetyl halide or the like in the presence of a tertiary amine, a condensation reagent or the like in an acetate solvent such as methyl acetate, ethyl acetate, n-propyl acetate, i-propyl acetate or t-butyl acetate; in a halogenated solvent such as dichloromethane, chloroform, bromoform, carbon tetrachloride or carbon tetrabromide; or in an ether solvent such as tetrahydrofuran, dioxane or ether. When the "halo" is bromo, it can be easily synthesized according to the following Scheme 2.

Scheme 2:

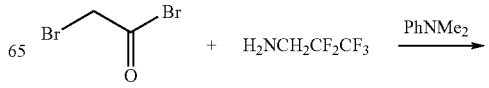

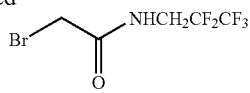

In a preferred embodiment, the reaction is carried out using bromoacetyl bromide as the haloacetyl halide, in an acetate solvent, preferably in ethyl acetate, in the presence of N,N-dimethylaniline at −20° C. to 0° C.

<Compound 5→Compound 6>

Compound 6 (the compound represented by the above-described Formula (2)) can be obtained by subjecting Compound 5 obtained in the previous step to desilylation reaction which is a deprotection step. By the desilylation reaction, TBS group, that is, tert-butyldimethylsilyl group is converted to a hydrogen atom. The desilylation reaction of Compound 5 can be carried out, for example, using an appropriate fluorine-containing reagent in a suitable solvent at a temperature between room temperature and reflux temperature for 10 minutes to 10 hours. Examples of the fluorine-containing reagent include tetra-n-butylammonium fluoride, hydrogen fluoride pyridine and the like. In this case, by further adding an organic acid such as acetic acid or benzoic acid, preferably acetic acid, to neutralize the basicity of the reaction solution, the substrates and products which are not stable under basic conditions may be stabilized, and adding the organic acid is preferred. Examples of the suitable solvents include amide solvents such as N,N-dimethylacetamide, N,N-dimethylimidazolidinone (DMI) and N,N-dimethylformamide (DMF); and ether solvents such as tetrahydrofuran, dioxane and ether. From the viewpoint of shortening the reaction time, amide solvents are preferred.

In a preferred embodiment, desilylation of Compound 5 is carried out using tetra-n-butylammonium fluoride, adding acetic acid or benzoic acid, preferably acetic acid in order to neutralize the reaction solution, in an amide solvent, preferably in N,N-dimethylacetamide, at a temperature of 60° C. to 150° C., preferably 90° C. to 120° C., for 6 to 12 hours.

From the viewpoint of the balance between the avoidance of side reactions and shortening of the reaction time, the amount of the tetra-n-butylammonium fluoride to be used is preferably 2 to 5 equivalents, more preferably 2.3 to 2.7 equivalents with respect to Compound 5. From the same viewpoint, the amount of the acetic acid to be used is preferably 1 to 5 equivalents, more preferably 1.5 to 2.5 equivalents with respect to Compound 5. The above-described steps from Compound 4 to obtainment of Compound 6 may be carried out as continuous reactions without isolating Compound 5.

In Scheme 1, the protective groups of the hydroxyl groups at 1- and 3-positions of Compounds 1 to 5 are specified to TBS group. However, even if silyl groups other than TBS group are employed, the same conversions as those of Compound 1→Compound 2, Compound 2→Compound 3, Compound 3→Compound 4, Compound 4→Compound 5, and Compound 5→Compound 6 can be attained. Compounds 1 to 5 in which the protective groups are not TBS groups can be obtained by deprotecting Compounds 1 to 5, respectively, and protecting the hydroxyl groups with the protective groups other than TBS groups. As for the deprotection and protection, after considering whether a functional group which is not appropriate to the reaction is contained or not, the method described in Greene and Wuts, "Protective Groups in Organic Synthesis", (Second Edition, John Wiley & Sons 1991) or the like may be referred to, and the method described in Example 4 of the present description may also be referred to. Compounds 1 to 5 having different substituted silyl groups at the 1- and 3-positions can be easily synthesized, utilized and deprotected by virtue of the difference in the reactivity between the hydroxyl groups at the 1- and 3-positions.

<Compound 6→Compound 7>

Compound 7 (the compound represented by the above-described Formula (6)) can be obtained by ring-opening reaction of the B-ring of the steroid skeleton of Compound 6 which is caused by the presence of the diene moiety. The opening of the B-ring of the steroid skeleton caused by the presence of the diene moiety can be carried out by, for example, irradiating Compound 6 with UV in a suitable solvent. The wavelength of UV to be radiated is not restricted as long as it is within the range which can be employed by those skilled in the art, and the wavelength is preferably 280 nm to 300 nm. As the solvent, ether solvents such as ether, dioxane, tetrahydrofuran and tetrahydropyrane; alcohol solvents such as methanol, ethanol, n-propanol, i-propanol and n-butanol; and acetate solvents such as methyl acetate, ethyl acetate, n-propyl acetate, i-propyl acetate and t-butyl acetate are preferred, and ethyl acetate is more preferred. Irradiation with UV may be carried out at a temperature between about −30° C. and +20° C. for 1 hour to 10 hours.

In a preferred embodiment, the ring-opening of Compound 6 is carried out by irradiating Compound 6 with UV in an acetate solvent, preferably in ethyl acetate, at −10° C. to 0° C. for 7 to 9 hours.

<Compound 7→Compound 8>

Compound 8 (the compound represented by the above-described Formula (1)) can be obtained by subjecting Compound 7 to an isomerization reaction. Isomerization reaction of Compound 7 is carried out, for example, in a suitable solvent at a temperature between room temperature and reflux temperature for 1 to 48 hours. The solvent is not restricted as long as it can dissolve the substrates and the products, and as long as it does not adversely affect their stabilities, and the solvent used in the reaction by UV irradiation may be used as it is. An acetate solvent is preferably used, and ethyl acetate is more preferably used.

In a preferred embodiment, the isomerization of Compound 7 is carried out by heating Compound 7 to reflux in ethyl acetate for 1 to 4 hours.

The above-described steps from Compound 6 to the obtainment of Compound 8 may be carried out in one pot as continuous reactions without isolating Compound 7.

EXAMPLES

An embodiment of the present invention will now be described in more detail by way of examples. In the following examples, NMR was measured using JEOL ECP-500 (Example 1) or JEOL EX-270 (Examples 3 and 4).

Example 1

Synthesis of (1S,3R,17R,20S)-1,3-bis(tert-butyldimethylsilyloxy)-17,20-epoxypregna-5-ene (Compound 2)

(17Z)-(1S,3R)-1,3-bis(tert-butyldimethylsilyloxy)pregna-5,17-diene (150 g) obtained according to the method described in Org. Process, Res. Dev., 2005, 9, 278-287 was dissolved in ethyl acetate (1.65 L), and m-chloroperbenzoic acid (81.6 g) was added thereto, followed by stirring the mixture at room temperature for 3 hours. Acetonitrile (2.25 L) was added to the reaction solution, and the reaction solution was cooled to 0° C. After collecting a precipitate by filtration, the precipitate was washed with acetonitrile and dried under reduced pressure to obtain (1S,3R,17R,20S)-1,3-bis(tert-butyldimethylsilyloxy)-17,20-epoxypregna-5-ene as white crystals (123 g; yield: 80%).

$^1$H-NMR (CDCl$_3$): δ 0.03 (s, 3H), 0.04 (s, 3H), 0.05 (s, 3H), 0.06 (s, 3H), 0.88 (s, 18H), 0.89 (s, 3H), 0.97 (s, 3H), 1.22 (m, 1H), 1.38 (d, J=6.0 Hz, 3H), 1.35-1.65 (m, 8H), 1.65-1.90 (m, 4H), 1.95-2.00 (m, 1H), 2.16-2.25 (m, 2H), 2.30 (m, 1H), 2.97 (q, J=5.5 Hz, 1H), 3.77 (q, J=1.8 Hz, 1H), 4.00 (m, 1H), 5.47 (m, 1H).

Example 2

Synthesis of (1S,3R,20S)-1,3-bis(tert-butyldimethylsilyloxy)-20-hydroxypregna-5,7,16-triene (Compound 4)

To (1S,3R,17R,20S)-1,3-bis(tert-butyldimethylsilyloxy)-17,20-epoxypregna-5-ene (100 g) obtained in Example 1, 2,2'-azobis(isobutyronitrile) (7.98 g) and γ-collidine (82.4 mL) were added, and the resulting mixture was stirred in n-heptane (1000 mL) at 75° C. for 15 minutes. After cooling the mixture to room temperature, a precipitate was removed by filtration, and the filtrate which was a solution in n-heptane was concentrated under reduced pressure. To the obtained concentrated residue containing γ-collidine, toluene (650 mL) and aluminum isopropoxide (3.64 g) were added, and the resulting mixture was heated to reflux for 2 hours. The reaction solution was cooled, and the organic layer was sequentially washed with aqueous hydrochloric acid, aqueous sodium bicarbonate and with water, followed by concentration under reduced pressure. After suspending the obtained concentrated residue in a mixed solvent of ethyl acetate, acetonitrile and triethylamine, a precipitate was collected by filtration, washed with acetonitrile, heat-dried under reduced pressure to obtain (1S,3R,20S)-1,3-bis(tert-butyldimethylsilyloxy)-20-hydroxypregna-5,7,16-triene as slightly yellow powder (37.5 g; yield: 37.7%).

The spectra data of the obtained (1S,3R,20S)-1,3-bis(tert-butyldimethylsilyloxy)-20-hydroxypregna-5,7,16-triene were identical with the spectra data of (1S,3R,20S)-1,3-bis(tert-butyldimethylsilyloxy)-20-hydroxypregna-5,7,16-triene described in Example 61 of WO 98/28266.

Example 3

Synthesis of 2-bromo-N-(2,2,3,3,3-pentafluoropropyl)acetamide (Compound 9)

2,2,3,3,3-Pentafluoropropylamine (produced by Synquest) (389 g) was dissolved in ethyl acetate (1.56 L), and N,N-dimethylaniline (316 g) was added thereto. After cooling the mixture to −10° C., bromoacetyl bromide (500 g) was added dropwise thereto, and the resulting mixture was stirred at a temperature between 10° C. and 0° C. for 2 hours. The organic layer was sequentially washed with aqueous hydrochloric acid, aqueous sodium bicarbonate and with brine, and dried over anhydrous magnesium sulfate, followed by concentration under reduced pressure to obtain 2-bromo-N-(2,2,3,3,3-pentafluoropropyl)acetamide (678 g) as a white powder.

$^1$H-NMR (CDCl$_3$) δ: 3.95 (s, 3H), 3.93-4.09 (m, 2H), 6.74 (bs, 1H).

Example 4

Synthesis of [{(1S,3R,20S)-1,3-dihydroxypregna-5,7,16-triene-20-yl}oxy]-N-(2,2,3,3,3-pentafluoropropyl)acetamide (Compound 6)

Under a nitrogen atmosphere, (1S,3R,20S)-1,3-bis(tert-butyldimethylsilyloxy)-20-hydroxypregna-5,7,16-triene (30.0 g) was dissolved in tetrahydrofuran (630 mL), and 0.55 mol/L potassium bis(trimethylsilyl)amide solution in toluene (244 mL) was added thereto dropwise at −10° C. After stirring the resulting mixture for 30 minutes, a solution of 2-bromo-N-(2,2,3,3,3-pentafluoropropyl)acetamide (15.9 g) obtained in Example 3 in tetrahydrofuran was added thereto dropwise over 20 minutes at −15° C., and the resulting mixture was continued to be stirred at the same temperature for 30 minutes. Aqueous ammonium chloride solution and ethyl acetate were added to the reaction solution to carry out extraction, and the organic layer was sequentially washed with water and brine, followed by concentration under reduced pressure. Further, ethyl acetate was removed by azeotropic distillation with methanol under reduced pressure. The obtained concentrated residue was then dissolved in N,N-dimethylacetamide (300 mL), and the resulting mixture was added to a solution of 75% aqueous tetra n-butylammonium fluoride solution (51 mL) and acetic acid (6.1 mL) in N,N-dimethylacetamide (60 mL), followed by stirring the resulting mixture at 100° C. to 105° C. for 7 hours. Ethyl acetate was added to the reaction mixture, and the organic layer was sequentially washed with water and brine, followed by concentration of the organic layer under reduced pressure. The obtained residue was recrystallized from 2-propanol and water to obtain [{(1S,3R,20S)-1,3-dihydroxypregna-5,7,16-triene-20-yl}oxy]-N-(2,2,3,3,3-pentafluoropropyl)acetamide as a gray powder (13.1 g; yield: 46.7%).

$^1$H-NMR (CDCl$_3$) δ: 0.06 (s, 6H), 0.07 (s, 3H), 0.11 (s, 3H), 0.86-0.92 (m, 21H), 0.95 (s, 3H), 1.37 (d, J=6.4 Hz, 3H), 2.79-2.92 (m, 1H), 3.67-3.74 (m, 1H), 3.87 (d, J=15.7 Hz, 1H), 3.92-4.13 (m, 5H), 5.36-5.44 (m, 1H), 5.58-5.67 (m, 2H), 6.87-6.96 (m, 1H); MS m/z: 748 (M$^+$), 73 (100%); UV λmax: 293, 281, 270, 261 nm; IR (neat): 2954, 2931, 2896, 1698, 1525, 1253, 1197, 1151, 1097 cm$^{-1}$.

Example 5

Synthesis of [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide (Compound 8)

[{(1S,3R,20S)-1,3-dihydroxypregna-5,7,16-triene-20-yl}oxy]-N-(2,2,3,3,3-pentafluoropropyl)acetamide obtained in Example 4 was dissolved in ethyl acetate (100 mL), and the resulting mixture was irradiated with UV under argon gas flow at a reaction temperature of −5° C. to 7° C. for 8 hours. The solution was then heated to reflux for 2 hours, and concentrated under reduced pressure.

The above-described reaction was repeated 10 times. The obtained concentrated residues were combined and purified by silica gel column chromatography (silica gel: Merck Silica Gel 60 (230-400 mesh); mobile phase: ethyl acetate/n-hexane=2/1), followed by concentration under reduced pressure to obtain 30.0 g of [{(5Z,7E)-(1S,3R,20S)-1,3-dihydroxy-9,10-secopregna-5,7,10(19),16-tetraen-20-yl}oxy]-N-(2,2,3,3-pentafluoropropyl)acetamide as a slightly yellow oil (yield: 25%).

The spectra data of the obtained [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide were identical with the spectra data of [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide described in Example 22(2) of WO 2001/096293.

<Comparison Between the Process of the Present Invention and Conventional Process>

In the production of Compound 8 from Compound 4, the process of the present invention has the following advantages over the conventional process:

Number of Steps: 5 steps in the conventional process (the steps described in Example 11(1), 17(1), 17(2), 22(1) and 22(2) in WO 2001/096293) versus 3 steps in the process of the present invention (the steps in Examples 3, 4 and 5 described above).

Number of Purification by Chromatography: 5 times in the conventional process (in each step mentioned in the item Number of Steps described above) versus once in the process of the present invention (only in Example 5 described above).

Yield: 5.7% in the conventional process (25% (Example 11(1) of WO 2001/096293)×69% (17(1) and (2))×33% (22(1) and (2)) versus 11.7% in the process of the present invention (46.7% (above-described Example 4)×25% (Example 5)).

INDUSTRIAL AVAILABILITY

By the process according to the present invention, practical and efficient synthesis of [{(5Z,7E)-(1S,3R,20S)-1,3-dihydroxy-9,10-secopregna-5,7,10(19),16-tetraen-20-yl}oxy]-N-(2,2,3,3,3-pentafluoropropyl)acetamide, which is useful as a pharmaceutical, is attained.

The invention claimed is:

1. A process for producing a compound represented by Formula (1):

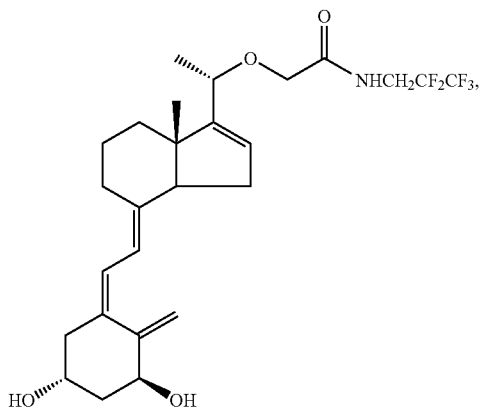

(1)

said process comprising the steps of:
irradiating a compound represented by Formula (2):

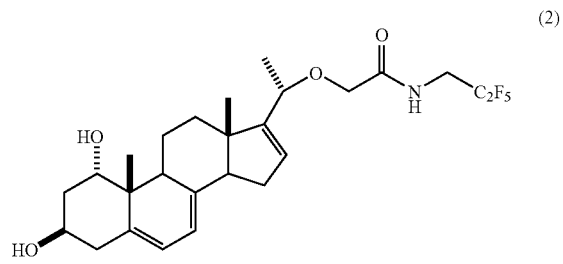

(2)

with UV to open the B-ring of the steroid skeleton of the compound; and isomerizing the resulting compound to obtain said compound of Formula (1), wherein said compound represented by Formula (2) is obtained by a process comprising the steps of:

subjecting a compound represented by Formula (3):

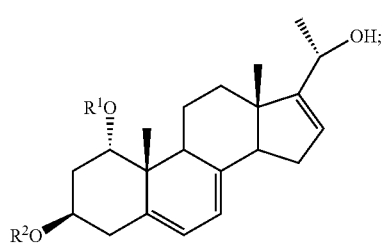

(3)

wherein $R^1$ and $R^2$, which may be the same or different, are each a substituted silyl group, to a formation of a conjugated diene in the B-ring of the steroid skeleton of the compound by brominating the methylene group at the 7-position in the B-ring of the steroid skeleton using a brominating agent in the presence of a radical initiator selected from benzoyl peroxide or 2,2'-azobis(isobutyronitrile), and then dehydrobrominating the resulting group in the presence of a base;

subjecting the resulting compound to a formation of an allyl alcohol moiety via ring-opening of the epoxy group in the presence of a Lewis acid to obtain a compound represented by Formula (4):

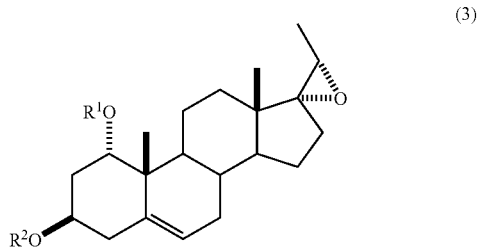

(4)

reacting the obtained compound with 2-bromo-N-(2,2,3,3,3-pentafluoropropyl) acetamide to obtain a compound represented by formula (5):

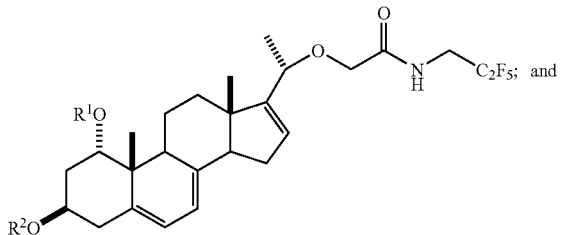

replacing $R^1$ and $R^2$ of the obtained compound with hydrogen atoms using a fluorine-containing reagent.

2. The process according to claim 1, wherein both of $R^1$ and $R^2$ are tert-butyldimethylsilyl groups.

3. The process according to claim 1, wherein said brominating agent is N-bromosuccinimide or 1,3-dibromo-5,5-dimethylhydantoin, said base is an organic amine selected from triethylamine, diethylamine, diisopropylamine, pyridine, dimethylaminopyridine or γ-collidine, or an inorganic alkali selected from sodium carbonate, potassium carbonate, sodium hydrogen carbonate, sodium hydroxide or calcium hydroxide, said Lewis acid is an aluminum trialkoxide, aluminum chloride or titanium chloride, and said fluorine-containing reagent is tetra-n-butylammonium fluoride or hydrogen fluoride pyridine.

4. The process according to claim 3, wherein said aluminum trialkoxide is aluminum isopropoxide.

5. A compound represented by Formula (3):

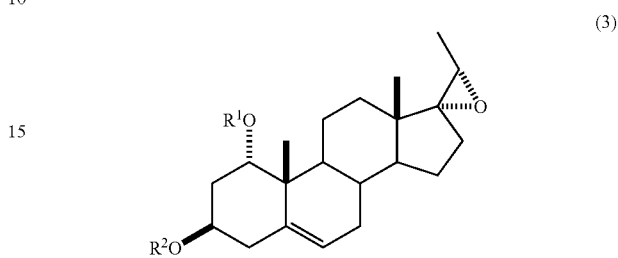

(wherein $R^1$ and $R^2$, which may be the same or different, are each a substituted silyl group).

6. The compound according to claim 5, wherein both of $R^1$ and $R^2$ are tert-butyldimethylsilyl groups.

* * * * *